(12) United States Patent
Eddy et al.

(10) Patent No.: US 11,187,689 B2
(45) Date of Patent: Nov. 30, 2021

(54) BIODEGRADABLE PARAMETER MONITOR

(71) Applicant: Carrier Corporation, Palm Beach Gardens, FL (US)

(72) Inventors: Renee A. Eddy, Manlius, NY (US); David C. Brondum, Cazenovia, NY (US); Mark E. Cywilko, Jamesville, NY (US); Richard P. Marcantonio, Liverpool, NY (US); James Taeckens, Manlius, NY (US); Jeffrey Allen Leshuk, Davis, CA (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 849 days.

(21) Appl. No.: 15/769,478

(22) PCT Filed: Oct. 4, 2016

(86) PCT No.: PCT/US2016/055307
§ 371 (c)(1),
(2) Date: Apr. 19, 2018

(87) PCT Pub. No.: WO2017/069939
PCT Pub. Date: Apr. 27, 2017

(65) Prior Publication Data
US 2018/0313803 A1  Nov. 1, 2018

Related U.S. Application Data

(60) Provisional application No. 62/243,845, filed on Oct. 20, 2015.

(51) Int. Cl.
*G01N 33/08* (2006.01)
*G01N 33/02* (2006.01)
(Continued)

(52) U.S. Cl.
CPC ............ *G01N 33/02* (2013.01); *G01N 33/15* (2013.01); *G01N 33/025* (2013.01); *G01N 33/12* (2013.01)

(58) Field of Classification Search
CPC ...... G01N 33/02; G01N 33/15; G01N 33/025; G01N 33/12
(Continued)

(56) References Cited

U.S. PATENT DOCUMENTS 7,492,326 B1     2/2009   Bodlovic et al.
2007/0245947 A1  10/2007  Riemelmoser
(Continued)

FOREIGN PATENT DOCUMENTS

WO   2011072349 A1   6/2011
WO   2014113460 A1   7/2014

OTHER PUBLICATIONS

Kuswandi, Bambang et al., "Smart Packaging: Sensors for monitoring of food quality and safety", Sens. & Instrumen. Food Qual. (2011), 5: pp. 137-146.
(Continued)

*Primary Examiner* — Md M Rahman
(74) *Attorney, Agent, or Firm* — Cantor Colburn LLP

(57) ABSTRACT

A method and apparatus for monitoring a product is provided, the sensor includes a first sensor element formed from a first biodegradable material and having a first sensor element height, wherein the first sensor element height changes in response to a first parameter of interest of the product.

11 Claims, 2 Drawing Sheets

(51) Int. Cl.
  *G01N 33/15* (2006.01)
  *G01N 33/12* (2006.01)

(58) Field of Classification Search
  USPC .......................................................... 356/55
  See application file for complete search history.

(56) References Cited

U.S. PATENT DOCUMENTS

| | | | | |
|---|---|---|---|---|
| 2009/0131773 | A1* | 5/2009 | Struve | G01N 33/54373 |
| | | | | 600/317 |
| 2010/0070068 | A1* | 3/2010 | Kaplan | B29D 11/0074 |
| | | | | 700/159 |
| 2010/0217556 | A1* | 8/2010 | Hohe | G01D 3/0365 |
| | | | | 702/104 |
| 2012/0262291 | A1 | 10/2012 | Bastide et al. | |
| 2013/0049932 | A1 | 2/2013 | Baym et al. | |
| 2013/0177393 | A1 | 7/2013 | Sishta | |
| 2014/0121557 | A1 | 5/2014 | Gannon et al. | |
| 2014/0140482 | A1* | 5/2014 | Lemaire | A61B 6/4452 |
| | | | | 378/62 |
| 2015/0002299 | A1 | 1/2015 | Sandvick | |
| 2015/0035680 | A1 | 2/2015 | Li et al. | |
| 2016/0050750 | A1* | 2/2016 | Rogers | H05K 3/285 |
| | | | | 361/767 |
| 2016/0195567 | A1* | 7/2016 | Tanaka | B81B 3/0072 |
| | | | | 73/514.32 |
| 2016/0375185 | A1* | 12/2016 | Meisberger | A61M 1/3627 |
| | | | | 250/341.7 |
| 2017/0045487 | A1* | 2/2017 | Bauer-Reich | H04B 7/1851 |
| 2017/0055890 | A1* | 3/2017 | Kube | H02J 7/025 |
| 2017/0112577 | A1* | 4/2017 | Bonutti | A61B 90/361 |

OTHER PUBLICATIONS

SA Frieght Council, "On Tarmac Temperature Control Aids", Report Prepared for The South Australian Freight Council Cold Chain Working Group, Apr. 2, 2008, available at: http://www.safreightcouncil.com.au/userfiles/docs/Resources&Reports/OnTarmac-CombinedReportSept08.pdf, 158 pages.

International Search Report and Written Opinion for application PCT/US2016/055307, dated Jan. 24, 2017, 10 pages.

Janssen et al. "Ethylene detection in fruit supply chains." Phil.Trans. R. Soc. A 372: Mar. 11, 2013. 2014. (21 pgs).

Jedermann et al., "Reducing food losses by intelligent food logistics." Phil. Trans. R. Soc. A372: Mar. 2, 2013. 20 pages. (20 pgs).

Jung, Scott, "NutriSmart: Edible RFID Tags for the Future", Medgadget, Jun. 1, 2011, 3 pages.

Lynch, Ken, "RFID Making Fresh Produce Cool", ThingMagic, available at: http://rfid.thingmagic.com/rfid-blog/bid/79059/RFID-Making-Fresh-Produce-Cool, Dec. 13, 2011, 13 pages.

Tao, Hu et al., "Silk-Based Conformal, Adhesive, Edible Food Sensors", Advanced Materials, vol. 24, No. 8, Jan. 20, 2012, pp. 1067-1072.

European Examination Report for Application No. 16794451.1; dated Sep. 17, 2021; 6 Pages.

* cited by examiner

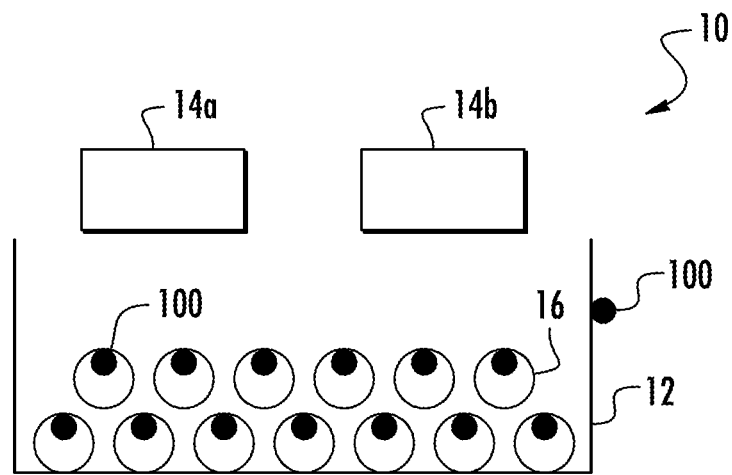
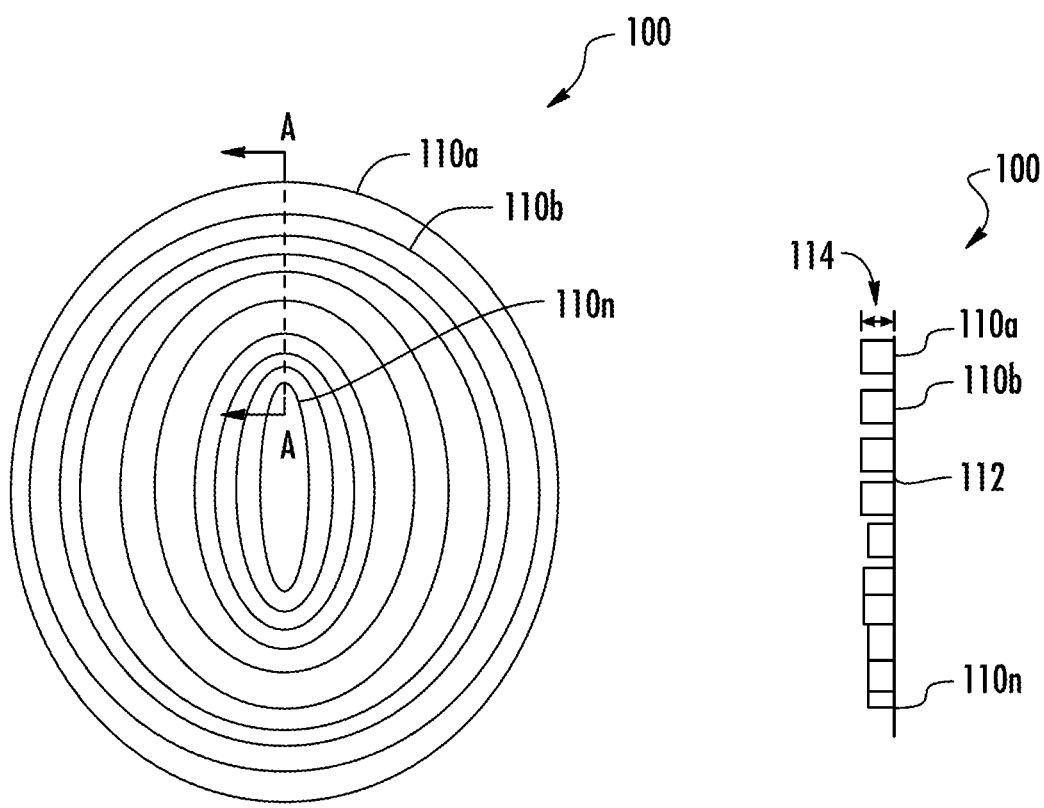
FIG. 1
FIG. 2A
FIG. 2B

BIODEGRADABLE PARAMETER MONITOR

DESCRIPTION OF RELATED ART

The subject matter disclosed herein relates to parameter monitoring, and to a system and a method for monitoring parameters via a biodegradable sensor.

Typically, cold chain distribution systems are used to transport and distribute temperature sensitive and perishable goods. For example, products such as food and pharmaceuticals may be susceptible to temperature, humidity, contaminants, and other environmental factors. Advantageously, cold chain systems allow perishable and environmentally sensitive goods to be effectively transported and distributed without damage or other undesirable effects.

Sensors are often used in cold chain distribution systems to monitor the conditions and integrity of the cold chain and consequently the goods transported. Current sensors may monitor parameters during certain portions of distribution, but may not track parameters at every point along distribution since sensors are often removed during transfers. A system and method that can provide monitoring of parameters via a biodegradable sensor is desired.

BRIEF SUMMARY

According to an embodiment, a sensor for monitoring a product is provided, the sensor includes a first sensor element formed from a first biodegradable material and having a first sensor element height, wherein the first sensor element height changes in response to a first parameter of interest of the product.

In addition to one or more of the features described above, or as an alternative, further embodiments could include that the first sensor element degrades to change the first sensor element height in response to the first parameter of interest.

In addition to one or more of the features described above, or as an alternative, further embodiments could include that the first sensor element degrades after a predetermined time.

In addition to one or more of the features described above, or as an alternative, further embodiments could include that the sensor has an elliptical shape.

In addition to one or more of the features described above, or as an alternative, further embodiments could include a degradable substrate, wherein the first sensor element is affixed to the degradable substrate.

In addition to one or more of the features described above, or as an alternative, further embodiments could include that the degradable substrate is a silk degradable substrate.

In addition to one or more of the features described above, or as an alternative, further embodiments could include that the first biodegradable material is conductive.

In addition to one or more of the features described above, or as an alternative, further embodiments could include that the first sensor element height provides a visual signal in response to the first parameter of interest.

In addition to one or more of the features described above, or as an alternative, further embodiments could include that the first parameter of interest is at least one of: a temperature value, an ethylene value, and a food borne pathogen value.

In addition to one or more of the features described above, or as an alternative, further embodiments could include at least one second sensor element formed from a second biodegradable material and having a second sensor element height, wherein the second sensor element height changes in response to a second parameter of interest.

In addition to one or more of the features described above, or as an alternative, further embodiments could include that the at least one second sensor element is disposed concentrically about the first sensor element.

According to an embodiment, a method for monitoring a product includes associating a first sensor element formed from a first biodegradable material with the product, changing a first sensor element height of the first sensor element in response to the first parameter of interest of the product, and degrading the first biodegradable material after a predetermined time.

In addition to one or more of the features described above, or as an alternative, further embodiments could include changing the first sensor element height by degrading the first sensor element in response to the first parameter of interest.

In addition to one or more of the features described above, or as an alternative, further embodiments could include transmitting the first parameter of interest via an RFID transmission, wherein the first biodegradable material is conductive and the first sensor element height corresponds to the RFID transmission.

In addition to one or more of the features described above, or as an alternative, further embodiments could include visually indicating the first parameter of interested via the first sensor element height.

Technical function of the embodiments described above includes a first sensor element formed from a first biodegradable material and having a first sensor element height, wherein the first sensor element height changes in response to a first parameter of interest of the product.

Other aspects, features, and techniques of the embodiments will become more apparent from the following description taken in conjunction with the drawings.

BRIEF DESCRIPTION OF THE SEVERAL VIEWS OF THE DRAWINGS

The subject matter is particularly pointed out and distinctly claimed in the claims at the conclusion of the specification. The foregoing and other features, and advantages of the embodiments are apparent from the following detailed description taken in conjunction with the accompanying drawings in which like elements are numbered alike in the several FIGURES:

FIG. 1 illustrates a schematic view of a parameter monitoring system;

FIG. 2A is a schematic view of a biodegradable sensor for use with the parameter monitoring system of FIG. 1;

FIG. 2B is a cross sectional view of the biodegradable sensor of FIG. 2A along section A-A.

DETAILED DESCRIPTION

Figure 3:
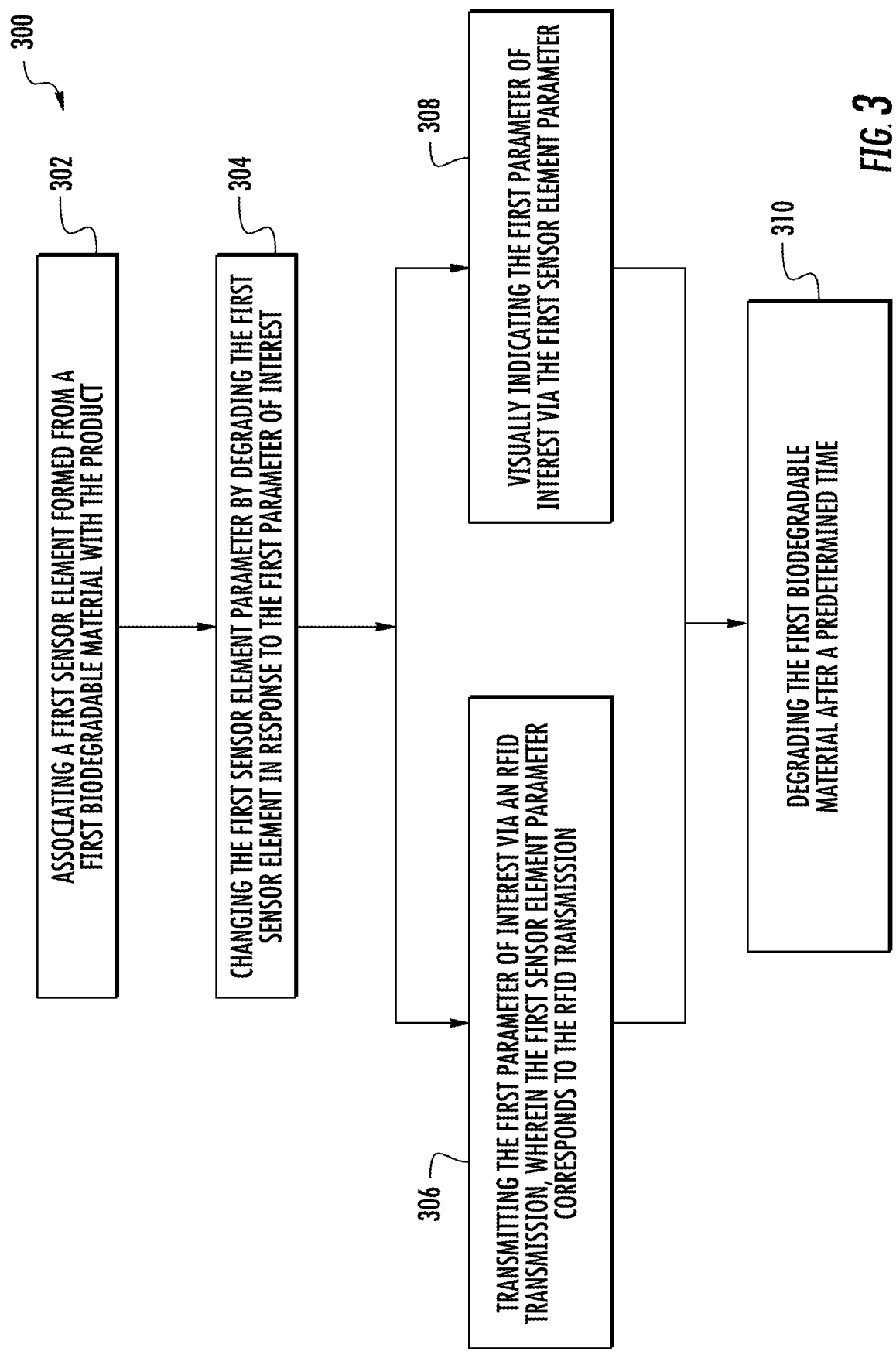
FIG. 3 is a flow diagram of a method of monitoring parameters using a biodegradable sensor.

Referring now to the drawings, FIG. 1 illustrates a schematic view of a parameter monitoring system 10 suitable for use with a cold chain transportation system or any other suitable distribution system. In the illustrated embodiment, the parameter monitoring system 10 includes products 16, a container 12, readers 14a, 14b, and sensors 100. In the illustrated embodiment, the parameter monitoring system 10 can be utilized to transport products, such as food, drugs, and other perishable products or goods from a source to a destination. Advantageously, the use of the parameter monitoring system 10 allows for certain parameters of products 16 to be monitored from when the sensor 100 is affixed to the product 16 to when it reaches the consumer.

In the illustrated embodiment, the product 16 can be any suitable product. In certain embodiments, the product 16 is a perishable product such as meat, fruit, vegetables, drugs, blood, etc. that may be transported via a cold chain system.

In the illustrated embodiment, the product 16 can be transported in a container 12. The product 16 can be stored within the container 12. In certain embodiments, the container 12 can be part of an environmental control system to provide desired environmental parameters, such as temperature, humidity, $CO_2$ level, and other conditions to the products 16 within the container 12.

In the illustrated embodiment, sensors 100 are affixed on products 16, containers 12, or any other suitable location. As described herein, the sensors 100 may be biodegradable sensors that are either degraded, destroyed, or edible by the time the target product 16 has reached the target consumer. In certain embodiments, the sensors 100 can be affixed to the products 16 in the field (e.g. produce at the time of harvesting or processing) to provide parameter monitoring for as long as possible. In certain embodiments, the sensors 100 can be affixed to all products 16, a selected group of the products 16, to container 12, or to a combination thereof. In the illustrated embodiment, the sensors 100 can monitor, communicate and otherwise indicate temperatures, chemical or gas presence, food borne pathogen presence, etc. In certain embodiments, the sensors 100 can monitor multiple parameters each. In certain embodiments, the sensor 100 can utilize conductive biodegradable materials to provide an RFID signal corresponding to a desired parameter value.

In the illustrated embodiment readers 14a and 14b can be utilized to read sensor 100 values reflecting parameters of interest of the products 16. In the illustrated embodiment, an RFID reader 14a is shown and an optical reader 14b is shown. In certain embodiments, the RFID reader 14a can energize a sensor 100 to receive a desired parameter value. The RFID reader 14a may be any suitable reader, including, but not limited to hand held readers, satellite readers, etc. In other embodiments, an optical reader 14b can visually scan the sensor 100 to receive the desired parameter value. The optical reader 14b can further be utilized with sensors 100 that provide RFID signals and sensors 100 that do not provide RFID signals. The optical reader 14b can be any suitable reader, include, but not limited to hand held readers, satellite readers, camera phones, tablets, etc. In certain embodiments, the readers 14a, 14b can transmit received parameter values to a central location for additional processing or logging.

Referring to FIGS. 2A and 2B, the biodegradable sensor 100 is illustrated. In the illustrated embodiment, the sensor 100 includes a plurality of biodegradable sensor elements 110a-110n. In the illustrated embodiment, the sensor 100 can include any suitable number of sensor elements 110a-110n corresponding to parameters or parameter ranges as described herein. Advantageously, the sensor 100 can be utilized as a passive storage device that can indicate and store parameters as shown by the relative geometry of the sensor elements 110a-110n.

In the illustrated embodiment, each sensor element 110a-110n is formed from a biodegradable material. In certain embodiments, the biodegradable material can be a protein based material that can break down, be edible, or otherwise harmless if encountered by a consumer. Further, the selected biodegradable materials for each sensor element 110a-110n can be selected to selectively degrade in response to a parameter of interest to provide a visual or electrical signal corresponding to the parameter of interest. In the illustrated embodiment, the sensor elements 110a-110n form ridges on the surface of the sensor 100. In the illustrated embodiment, the sensor elements 110a-110n can be formed in concentric shapes. In certain embodiments, the sensor elements 110a-110n are formed in elliptical shape.

In the illustrated embodiment, each of the sensor elements 110a-110n is associated with and encodes a specific parameter such as temperature, humidity, gas presence (such as carbon dioxide and ethylene), bacterial presence (such as *E. coli*), viral presence, ambient light, etc. Accordingly, the material selected for each desired parameter is a material that may degrade (or otherwise be geometrically altered) in response to the desired parameter. In the illustrated embodiment, each sensor element 110a-110n can alter its geometry in response to the parameter of interest for that respective sensor element 110a-110n. For example, the geometry of the sensor elements 110a-110n can be changed such that the height 114 of a sensor element 110a-110n can change in response to a parameter change. In the illustrated embodiment, the height 114 of a respective sensor element 110a-110n can be altered by degrading in response exposure to the corresponding parameter. In other embodiments, the geometry of the sensor elements 110a-110n can be altered via melting or spreading in response to exposure to the corresponding parameter.

In the illustrated embodiment, multiple sensor elements 110a-110n can be utilized for a single sensor 100 to monitor and encode multiple parameters of interest. Various sensor elements 110a-110n of varying chemical composition can monitor different parameters or ranges of the same parameter. For example, a first sensor element 110a could monitor temperature within a range of 50 degrees F. to 85 degrees F., wherein the experienced temperature corresponds to the observed height 114 within the range of the sensor element 110a, and another sensor element 110b could monitor temperature within a range of 85 degrees F. to 120 degrees F., wherein the experienced temperature corresponds to the observed height 114 within the range of the sensor element 110b. Further, another sensor element 110n could monitor the presence of *E. coli*, etc. In certain embodiments, the sensor elements 110a-110n can be utilized to encode and monitor ranges, such as temperature ranges, or excursions, such as an unacceptable food borne pathogen level or a high temperature.

In certain embodiments, the sensor elements 110a-110n correspond the exposure to a parameter to the height 114 of the sensor elements 110a-110n, allowing for a visual indicator corresponding to each parameter of interest. In certain embodiments, the sensor elements 110a-110n can further include markings, indexes, references or other visual indicators to facilitate human or machine reading of the sensors 100. In certain embodiments, dedicated readers or multipurpose devices can determine the values of the parameters of interest by utilizing a visual scan.

In other embodiments, the biodegradable material of each of the sensor elements 110a-110n can include or be formed from a conductive material. Therefore, in certain embodiments, the signal or impedance of the sensor elements 110a-110n can change as the height 114 or geometry changes in response to exposure to a corresponding parameter. In certain embodiments, dedicated readers of multipurpose devices can determine the values of the parameters of interest by utilizing an RFID transmission.

In the illustrated embodiment, the sensor elements 110a-110n can be affixed to a substrate 112 to hold the sensor elements 110a-110n together. In certain embodiments, the substrate 112 is also degradable. The substrate 112 can be a silk based substrate. In certain embodiments, the sensor 100 can be configured to degrade not only in response to parameters of interest, but the sensor 100 can also degrade after a predetermined amount of time.

FIG. 3 illustrates a method 300 to monitor parameters of a product. In operation 302, a first sensor element formed from a first biodegradable material is associated with the product. In the illustrated embodiment, sensors are affixed on products, containers, or any other suitable location. In certain embodiments, the sensors can be affixed to the products in the field (e.g. produce at the time of harvesting or processing) to provide parameter monitoring for as long as possible.

In operation 304, the first sensor element height is changed by degrading the first sensor element in response to the first parameter of interest. In the illustrated embodiment, each of the sensor elements is associated with and encodes a specific parameter such as temperature, humidity, gas presence (such as carbon dioxide and ethylene), bacterial presence (such as *E. coli*), viral presence, ambient light, etc. In the illustrated embodiment, each sensor element can alter its geometry in response to the parameter of interest for that respective sensor element.

In operation 306, the first parameter of interest is transmitted via an RFID transmission, wherein the first biodegradable material is conductive and the first sensor element height corresponds to the RFID transmission. In certain embodiments, the RFID reader can energize a sensor to receive a desired parameter value.

In operation 308, the first parameter of interest is visually indicated via the first sensor element height. In certain embodiments, the sensor elements can further include markings, indexes, references or other visual indicators to facilitate human or machine reading of the sensors.

In operation 310, first biodegradable material is degraded after a predetermined time. In certain embodiments, the sensor be configured to degrade not only in response to parameters of interest, but the sensor can also degrade after a predetermined amount of time.

The terminology used herein is for the purpose of describing particular embodiments only and is not intended to be limiting of the embodiments. While the description of the present embodiments has been presented for purposes of illustration and description, it is not intended to be exhaustive or limited to the embodiments in the form disclosed. Many modifications, variations, alterations, substitutions or equivalent arrangement not hereto described will be apparent to those of ordinary skill in the art without departing from the scope and spirit of the embodiments. Additionally, while various embodiments have been described, it is to be understood that aspects may include only some of the described embodiments. Accordingly, the embodiments are not to be seen as limited by the foregoing description, but are only limited by the scope of the appended claims.

What is claimed is:

1. A sensor for monitoring a product comprising:
   a first sensor element formed from a first biodegradable material and including a first ridge having a first sensor element height, wherein the first sensor element height of the first ridge changes in response to a first parameter of interest of the product;
   wherein the first sensor element degrades to change the first sensor element height of the first ridge in response to the first parameter of interest.

2. The sensor of claim 1, wherein the first sensor element degrades after a predetermined time.

3. The sensor of claim 1, wherein the sensor has an elliptical shape.

4. The sensor of claim 1, further comprising a degradable substrate, wherein the first sensor element is affixed to the degradable substrate.

5. The sensor of the claim 4, wherein the degradable substrate is a silk degradable substrate.

6. The sensor of claim 1, wherein the first biodegradable material is conductive.

7. The sensor of claim 1, wherein the first sensor element height provides a visual signal in response to the first parameter of interest.

8. The sensor of claim 1, wherein the first parameter of interest is at least one of: a temperature value, an ethylene value, and a food borne pathogen value.

9. The sensor of claim 1, further comprising:
   at least one second sensor element formed from a second biodegradable material and including a second ridge having a second sensor element height, wherein the second sensor element height of the second ridge changes in response to a second parameter of interest, the second parameter of interest different than the first parameter of interest.

10. The sensor of claim 9, wherein the at least one second sensor element is disposed concentrically about the first sensor element.

11. A method for monitoring a product, comprising: associating a first sensor element formed from a first biodegradable material with the product, the first sensor element including a first ridge having a first sensor element height, wherein the first sensor element height of the first ridge changes in response to a first parameter of interest of the product; allowing the first biodegradable material to degrade after a predetermined time such that the first sensor element height of the first ridge decreases; scanning the first sensor element including the first ridge to determine a first parameter of interest.

\* \* \* \* \*